United States Patent [19]

Hulette et al.

[11] Patent Number: 5,236,666
[45] Date of Patent: Aug. 17, 1993

[54] TEMPERATURE REGULATION IN A SAMPLE HANDLING SYSTEM FOR AN OPTICAL MONITORING SYSTEM

[75] Inventors: William C. Hulette, Hillsborough, N.C.; Joseph G. Karp, St. Charles, Ill.; Janet B. Callahan, Chapel Hill; Paul J. Braun; Stephen G. Richardson, both of Durham, all of N.C.

[73] Assignee: Akzo N.V., LS Arnhem, Netherlands

[21] Appl. No.: 833,950

[22] Filed: Feb. 11, 1992

Related U.S. Application Data

[63] Continuation of Ser. No. 443,951, Dec. 1, 1989, abandoned.

[51] Int. Cl.5 .............................................. G01N 35/04
[52] U.S. Cl. ...................................... 422/65; 422/63; 422/67; 422/82.05; 422/100; 436/47; 436/165; 436/180; 435/809
[58] Field of Search .................. 422/63, 65, 67, 82.05, 422/82.12, 109, 100; 436/47, 165, 180; 435/290, 809, 808

[56] References Cited

U.S. PATENT DOCUMENTS

| | | | |
|---|---|---|---|
| 4,483,927 | 11/1984 | Takekawa | 436/43 |
| 4,625,096 | 11/1986 | Fletcher | 422/65 |
| 4,647,431 | 3/1987 | Sekine et al. | 422/63 |
| 4,708,886 | 11/1987 | Nelson | 422/72 |
| 4,727,032 | 2/1988 | Baisch et al. | 422/65 |
| 4,731,225 | 3/1988 | Wakatake | 422/65 |
| 4,844,868 | 7/1989 | Rokugawa | 422/64 |
| 4,919,887 | 4/1990 | Wakatake | 422/67 |
| 5,038,852 | 8/1991 | Johnson et al. | 422/116 |

Primary Examiner—James C. Housel
Assistant Examiner—Long V. Le
Attorney, Agent, or Firm—Spencer, Frank & Schneider

[57] ABSTRACT

An arrangement is provided for temperature regulating a fluid sample in a cuvette transported through various stations of an automated system for optically monitoring the sample in the cuvette. A track guides the cuvette through the various stations of the optical monitoring system. The sample is in heat exchange relationship with the track by way of the cuvette. A drive unit drives the cuvette along the track. A cooling unit cools a first portion of the track. A heating unit heats a second portion. A heat flow restriction device restricts heat flow between the first and second portions of the track.

4 Claims, 5 Drawing Sheets

TEMPERATURE REGULATION IN A SAMPLE HANDLING SYSTEM FOR AN OPTICAL MONITORING SYSTEM

CROSS REFERENCE TO RELATED APPLICATIONS

This application is a continuation-in-part application of U.S. patent application Ser. No. 07/443,951, now abandoned, the disclosure of which is incorporated herein by reference.

This application is additionally related to the following copending U.S. Patent Applications, which are owned by the Assignee of the present Application, and the disclosures of which are incorporated herein by reference:

(1) Ser. No. 07/443,952, to Swope et al entitled "Multichannel, Optical Monitoring Systems" now U.S. Pat. No. 5,002,392;
(2) Ser. No. 07/443,956, to Karp et al entitled "Cuvette and Linear Drive Mechanism Therefor" now U.S. Pat. No. 5,040,894; and
(3) Ser. No. 07/443,954, to Hoffman et al entitled "Apparatus and Method for Cleaning Reagent Delivery Probes" now U.S. Pat. No. 4,989,623.

BACKGROUND OF THE INVENTION

The present invention relates to a sample handling system for an optical monitoring system, and more particularly, to an automated sample handling system for an optical evaluation instrument which includes optical monitoring means for monitoring changes in optical characteristics of a reaction volume in a reaction well of a cuvette when the cuvette is positioned in the optical path of the optical monitoring means.

Automated sample handling systems for optical evaluation instruments are known which automatically dispense patient fluid samples, such as blood plasma, along with reagents and other additives, into the reaction well of a cuvette which is then automatically positioned in the optical path between a light source and a detector for monitoring changes in the optical characteristics in the reaction volume of the cuvette as the reaction is allowed to progress over time. Such instruments are useful in the field of biochemical analysis for measuring blood plasma coagulation time and performing factor and other chromogenic assays and related analyses.

An automated sample handling system in an optical evaluation system of this type is described by Nelson L. Alpert, Ph.D., in the Spotlight section of "CIS", a publication by Clinical Instruments Systems, Inc., Volume 9, number May, 5, 1988, pages 1 to 7. The system described by Alpert is based upon principles of centrifugal analysis whereby patient plasma samples and reagents are automatically dispensed into radial chambers of a rotor. The chambers serve both as reaction vessels and as photometric cuvettes. The cuvettes spin through the optical path of a fixed photometer. An optical beam illuminates each cuvette from beneath the rotor and a detector above the rotor collects the light signals from each of the cuvettes in sequence. The optical data are collected and analyzed by the system's computer.

In this system, the automatic dispensing of samples and reagents is accomplished by a single probe arm which has sample and reagent probes. At the beginning of a run, the probe arm rotates to aspirate a sample on a sample tray which accommodates 20 sample cups, one of which is reserved for a calibration plasma or a normal pool sample, and a second for diluent. This leaves room for as many as 18 samples. The rotor likewise has 20 reaction vessels. After aspirating a sample, the probe arm rotates to a reagent reservoir for a test programmed for the sample just aspirated and aspirates a reagent from the reservoir. There are three reagent reservoirs each comprised of a reagent cup which are maintained at about 15° C. The probe arm is next positioned over a reaction vessel in the rotor to dispense both the sample and reagent into the reaction vessel. After a washing process the probe arm repeats the sequence for dispensing sample and reagent into respective reaction vessels until all of the reaction vessels for the particular run are loaded. The rotor is then spun up and the reactants in each radial pathway are spun to a chamber near the circumference of the rotor where the samples spin through the optical path of the photometer. The analytical time after a rotor receives samples and reagents is the same whether a single sample is run singly or in duplicate or the rotor is completely filled with samples. That is, a whole batch of up to 18 samples is analyzed in the same time as a single sample.

While the above-described system provides a certain amount of automation and flexibility to the handling of samples in an optical evaluation instrument, it still has a number of drawbacks. To begin with, the plasma, which is prepared in a separate centrifugation process, must first be transferred from the centrifugated test tube into a sample cup of the sample tray. When the centrifugated test tube comprises an evacuated sample collection tube sealed by a septum, which is now common, this requires either removing the septum or piercing the septum and aspirating a desired amount of plasma out of the collection tube and then dispensing the aspirated plasma into a sample cup of the sample tray. This must be done for each patient plasma sample loaded into the sample tray. This process poses contamination problems, both to the patient samples and to the clinical worker performing the transfer process. It would therefore be preferable if a sample handling system could be designed to eliminate the above-described transfer process by incorporating a mechanism which could remove a patient plasma sample from an evacuated and spun down test tube containing a patient's blood plasma with the septum intact and transfer the patient plasma sample directly to the reaction well of a cuvette without human intervention.

Another drawback of the above-described system is its limited throughput. The rotor only contains 20 reaction vessels, and only a maximum of 18 of these reaction vessels can be used for patient samples. Additionally, only one type of test may be performed on any one run of the rotor. It often occurs, therefore, that some of the available reaction vessels remain unused on a given run. Further, an operator must program the instruments' computer with the identification of each sample and the test to be performed, which further adds to the total analysis time.

A further drawback of the above-described system is that it essentially requires the attendance of a full-time operator. Because the system only runs a maximum of 18 patient samples during any one run, an operator must be present at the conclusion of each run, which may take anywhere from approximately three to eleven minutes, depending on the test being performed, to replace the sample tray with a new sample tray and set the machine up for the next run. It would be desirable to have a sample handling system with equivalent or better throughput of patient samples with walk-away automation on the order of one or more hours, thereby freeing the operator to perform other tasks.

Yet, another drawback of the above-described system is that it can accommodate a relatively limited number reagents at any one time and further, only the reagents are temperature controlled. The lack of temperature control for the patient samples provides an inherent limitation on the number of samples that can be run at any one time since the patient samples must be kept cool just prior to the analysis, at which time the patient samples must be brought up to body temperature.

SUMMARY OF THE INVENTION

It is therefore an object of the invention to provide a sample handling system for an optical evaluation instrument that can handle a high throughput of patient samples with a high degree of versatility, adaptability and reliable automation.

It is a further object of the invention to provide walk-away automation for a sample handling system for an optical evaluation instrument, once patient samples still sealed in the original evacuated collection tube are loaded into the system.

It is another object of the invention to provide improved temperature regulation of patient samples in an automated sample handling system for an optical evaluation instrument.

The above and other objects are accomplished according to the invention in the context of a sample handling system for an optical evaluation instrument which includes optical monitoring means having an optical path for monitoring changes in optical characteristics of a reaction volume in a reaction well of a cuvette when the cuvette is positioned in the optical path of the optical monitoring means, including: cuvette storage for storing a plurality of cuvettes, each cuvette containing a plurality of reaction wells; a temperature controlled housing for storing a plurality of reagent containers, each containing a respective reagent, and a plurality of sample collection tubes, each containing a fluid sample and presenting a optically readable code identifying the sample and a test to be performed on the sample; a programming station including for optically reading the code presented by the respective collection tubes for programming the instrument with a test to be performed on the sample contained in a respective one of the sample collection tubes; a sample insertion station including a mechanism for aspirating sample from the sample collection tubes and for dispensing the aspirated samples into respective ones of the reaction wells of the cuvettes; a reagent station, including a reagent handling mechanism for aspirating selected amounts of selected reagents from selected reagent containers and for dispensing the aspirated reagents into a reaction well of a cuvette according to the programmed test for the sample in that reaction well, the reagent and sample in the reaction well forming a reaction volume which exhibits optical characteristics to be monitored by the instrument; a first transporting device for transporting the sample collection tubes in seriatim first to the programming station and then to the sample insertion station; and a second transporting device for transporting the cuvettes through the sample insertion station, the reagent station, and on to the optical monitoring device where the optical characteristics of the reaction volume of the in the respective reaction wells can be monitored.

According to a preferred embodiment of the invention, the sample collection tubes are evacuated and sealed by a septum, and a piercer is provided at the sample insertion station for piercing the septums of the respective evacuated sampling tubes to permit access by a sampling probe to aspirate sample from the sample collection tubes.

According to another aspect of the invention, the temperature controlled housing maintains the temperature of the evacuated collection tubes and the reagent containers between 4° C. and 8° C. Further, the second transporting device preferably includes a linear track for guiding the cuvettes and a drive mechanism for periodically moving the cuvettes along the track in discrete increments. Preferably, the drive mechanism includes a lead screw and the cuvettes are each shaped for engaging the lead screw for being driven along the linear track in the manner described in the above referenced Karp et al application. According to yet a further aspect of the invention the cuvette storage includes a device for removing the cuvettes from the storage and placing the cuvettes onto the linear track. Additionally, the first transporting device preferably includes a plurality of shuttles each for holding a plurality of sample collection tubes and means for moving the shuttles through the programming and sample insertion stations.

According to yet another aspect of the invention, a method is provided for handling samples using the foregoing sample handling system.

According to another respect of the invention there is provided an arrangement for temperature regulating a fluid sample in a cuvette transported through various stations of an automated system for optically monitoring the sample in the cuvette, comprising: a track for guiding the cuvette through the various stations of the optical monitoring system, the sample being in heat exchange relationship with the track by way of the cuvette; drive means for driving the cuvette along the track; cooling means for cooling a first portion of the track; heating means for heating a second portion of the track; and heat flow restriction means for restricting heat flow between the first and second portions of the track.

Other details and advantageous features of the invention will become apparent from the following description when taken in connection with the accompanying drawings and the appended claims.

DETAILED DESCRIPTION OF THE PREFERRED EMBODIMENT

Figure 1:
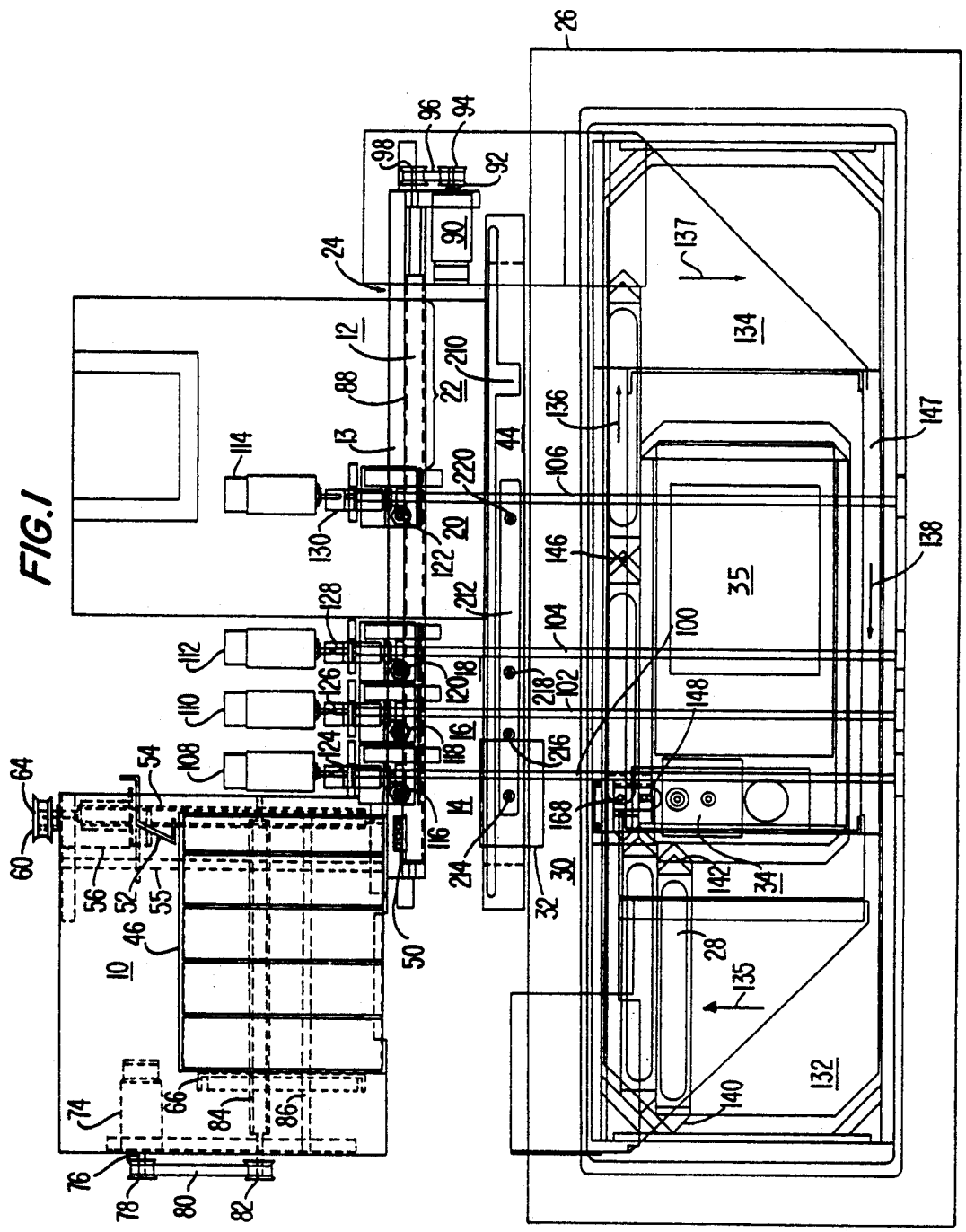
FIG. 1 is a schematic top elevation of a sample handling system in a optical evaluation instrument according to the invention.

Referring to FIG. 1, there is shown an optical evaluation instrument incorporating a sample handling system according to the invention. The principal elements of the sample handling system include a cuvette storage and loading mechanism 10, for supplying cuvettes individually to a cuvette transport mechanism 12, which advances the cuvettes along a linear track 13 through a sample insertion station 14, a plurality of reagent insertion stations 16, 18 and 20, an optical monitoring station 22 and finally, to a cuvette disposal station 24. The sample handling system additionally includes a refrigerated housing 26, for storing a plurality of evacuated collection tubes (not shown), which are transported via shuttles 28 through a programming station 30, including a bar code reader 32, for reading a preprinted bar code printed on the side of each evacuated collection tube identifying the test sample and the test to be performed, and onto sample insertion station 14, which includes a piercer 34, for piercing the septum of an evacuated collection tube for allowing a sample probe 36 (see FIG. 2) to be lowered into the sample collection tube for aspirating a fluid sample which is to be ejected into a reaction well of a cuvette located at sample insertion station 14, as described in greater detail herein below. Refrigerated housing 26, additionally encloses a reagent chamber 35, which stores a plurality of reagent containers (see FIGS. 5 and 6), which can be accessed by reagent probes 38, 40 and 42 (see FIG. 2), for aspirating selective reagents and injecting them into reaction wells located at the respective reagent insertion stations 16, 18 and 20. As used herein, reagents include any reagent, diluent, buffer, or activator which is required for any given biochemical test being performed on the patient sample according to a preprogrammed test protocol. A probe washing station 44, is provided for washing the sample and reagent probes after each dispensing action.

Figure 4:
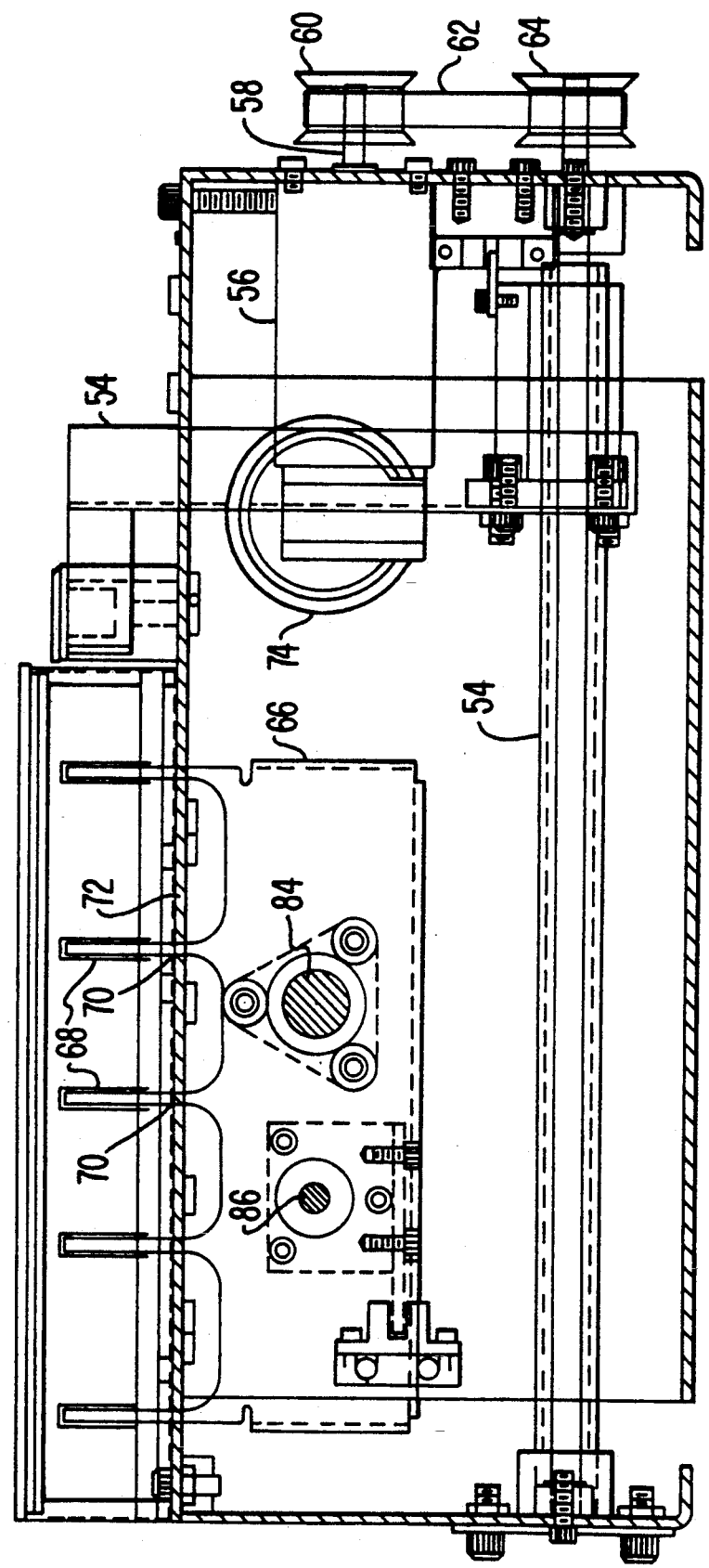
FIG. 4 is a schematic right-side elevation of the cuvette storage device of FIG. 1.

Referring to FIGS. 1 and 4, cuvette storage device 10 includes a cassette frame 46, for receiving a cassette of cuvettes arranged in the cassette in columns parallel to the right and left hand sides of frame 46 in FIG. 1. The cassettes are preferably of the type described in U.S. Pat. No. 5,040,894 to Karp et al. cited above. A plan view of one such cuvette 50 is seen in a loading position with respect to cuvette transport mechanism 12. A pusher arm 52, driven by a lead screw 54, loads cuvettes onto cuvette transport mechanism 12. A motor 56, whose shaft 58, is connected with a pulley 60 rotates a driving belt 62 which turns a pulley 64 for driving lead screw 54. A fixed guide rod 55 is provided in the usual manner for providing guidance and additional support for pusher arm 52. After a column of cuvettes is completely loaded onto cuvette transport mechanism 12, pusher arm 52 is retracted and a new column of cuvettes is moved rightwardly (in FIG. 1) by way of a cassette column drive mechanism to be in line with pusher arm 52. The cassette column drive mechanism includes a plate 66, provided with fingers 68, extending through slots 70 in a bottom support 72 of cassette frame 46. A rectangular plate (now shown), is positioned between fingers 68 and the left-hand most column of cassettes (not shown) in frame 46 for pushing the cassette columns in a rightward direction in FIG. 1. Plate 66 is driven by way of a motor 74 whose shaft 76 is connected to a pulley 78 which turns a driving belt 80 connected to a further pulley 82 which turns a lead screw 84, whose threads engage with plate 66. A fixed guide rod 86, is provided parallel to lead screw 84, for guiding plate 66 in the usual manner.

Cuvette transport mechanism 12, includes a lead screw 88, which is driven by way of a motor 90 whose shaft 92 is connected to a pulley 94 for turning a belt 96 which is connected for driving a pulley 98 connected to lead screw 88. The cuvettes are each provided with an engaging means, such as a rib having the same pitched angle as the threads of lead screw 88 which engage the lead screw threads when placed in a loading position by pusher arm 52. A cuvette 50 is shown in the loading position engaging lead screw 88. Cuvettes of this type, which desirably have four reaction wells, as shown by cuvette 50, are disclosed in the aforementioned U.S. Pat. No. 5,040,894, to Karp et al. Once engaged with lead screw 88, the cuvettes are advanced in a rightward direction in FIG. 1 along linear track 13 through the various stations as described herein for injecting a sample volume and reagents to create a reaction volume to be optically monitored at the optical monitoring station.

Linear track 13 is preferably made of a single piece of aluminum having a smooth upper surface on which the cuvettes can slide without interference. Desirably, linear track 13 is temperature controlled for controlling the temperature of the contents of the cuvette reaction wells, which contents are in heat exchange relationship with the track through the cuvettes. For this purpose, linear track 13 is cooled on the left side of a heat flow restriction 15 shown in FIG. 2 by way of, for example a Peltier device (not shown) to maintain the temperature of the reaction well contents at about 15° C. On the right hand side of heat flow restriction 15, linear track 13 is heated by way of a heating element 17, such as a resistive heat tape, applied to the under side of the linear track for maintaining the temperature of the reaction well contents at body temperature. Preferably, heat flow restriction 15 is formed by an elongated notch in the underside of linear track 13 so as to reduce the cross section of the track in the region of the notch and thus correspondingly reduce the heat flow by an effective amount from the heated portion to the cooled portion of the track. The upper surface of the track in the region of the notch remains smooth and continuous so as not to present any interference with the cuvettes sliding thereon. Control signals for controlling motors 56, 74, and 90, for turning respective lead screws 54, 84 and 88, to accomplish the required incremental movements of pusher arm 52, plate 66, and cuvette 50, respectively, are received from a central controller (not shown) of the instrument in a manner well understood by those skilled in the art.

Sample probe 36, and reagent probes 38, 40 and 42 are controllably moved along a horizontal path by way of respective lead screws 100, 102, 104 and 106, driven by respective motor assemblies 108, 110, 112 and 114. Vertical movement for lowering and raising sample probe 36, and reagent probes 38, 40 and 42, is accomplished by way of respective vertical gear racks 116, 118, 120 and 122, driven by corresponding vertical motor and pinion assemblies 124, 126, 128, and 130, respectively. Horizontal lead screw motors 108, 110, 112 and 114, and vertical rack and pinion motors 124, 126, 128 and 130, are selectively controlled by signals received from the instrument controller (not shown) for controlling the horizontal and vertical movement of the respective probes for aspirating and dispensing sample and reagents according to the test protocol identified from the bar code of a given sample collection tube read by bar code reader 32. Sample and reagent aspiration and dispensing by probes 36, 38, 40 and 42 is accomplished by way of positive displacement pumps (not shown) connected to the respective probes in a manner understood by those skilled in the art.

Refrigerated housing 26, comprises a double walled insulated enclosure 131, and a cooling system 133, preferably of the ducted type, for circulating cooling air within housing 26 for maintaining the temperature of sample collection tubes (not shown) mounted in shuttles 28 and reagents in reagent chamber 35 at a temperature between 4° and 8° C.

Referring to the plan view shown in FIG. 1, refrigerated housing 26, has left and right chambers 132 and 134, respectively, connected by passages 146 and 147 for storing and transporting shuttles 28, which are caused to move in a clockwise direction, as shown by arrows 135 to 138. Each shuttle 28 is provided with means for carrying a plurality of evacuated sample collection tubes of the type, for example, made by Beckton Dickinson of Rutherford, N.J., and sold under the brand name Vacutainer. The configuration of shuttles 28, and the mechanism for transporting the shuttles is disclosed in detail, for example, in U.S. Pat. No. 3,418,084 to Allington.

Briefly, each shuttle 28 has complimentary camming surfaces 140 and 142 formed at the opposite ends thereof. Shuttles 28 are disposed in rows in the respective chambers 132 and 134. A drive mechanism (not shown) comprising gears which mesh with gear tracks 29 on the bottom of the shuttles 28 (FIG. 2) drive the shuttles through passages 146 and 147 in opposite directions. The shuttle drive mechanism causes a driven shuttle to push the shuttle in front of it and the camming surfaces effect a lateral displacement in the manner described by the above-referenced patent to Allington.

The shuttles are transported, one behind the other, in passages 146, so that the evacuated collection tubes are passed first through programming station 30 where bar code reader 32 reads a previously-applied bar code on the side of the evacuated collection tube to identify the sample and the test to be performed. The information read by bar code reader 32 is fed to the instrument controller (not shown) for controlling subsequent movement of the sample and reagent probes for filling a reaction well of a cuvette transported by cuvette transporting mechanism 12 through the respective sample and reagent stations.

After having its bar code read, the evacuated collection tube is moved, by way of the shuttle and shuttle drive mechanism, a precise distance to place the evacuated collection tube in line with piercer 34. The precise positioning of the shuttle is accomplished by way of an electro-optical sensing mechanism 148 (FIG. 1), which passes a sensing beam through spaced passages 150 (FIG. 2), provided in the base of shuttles 28, for sensing when the shuttle is in the appropriate position.

Figure 3:
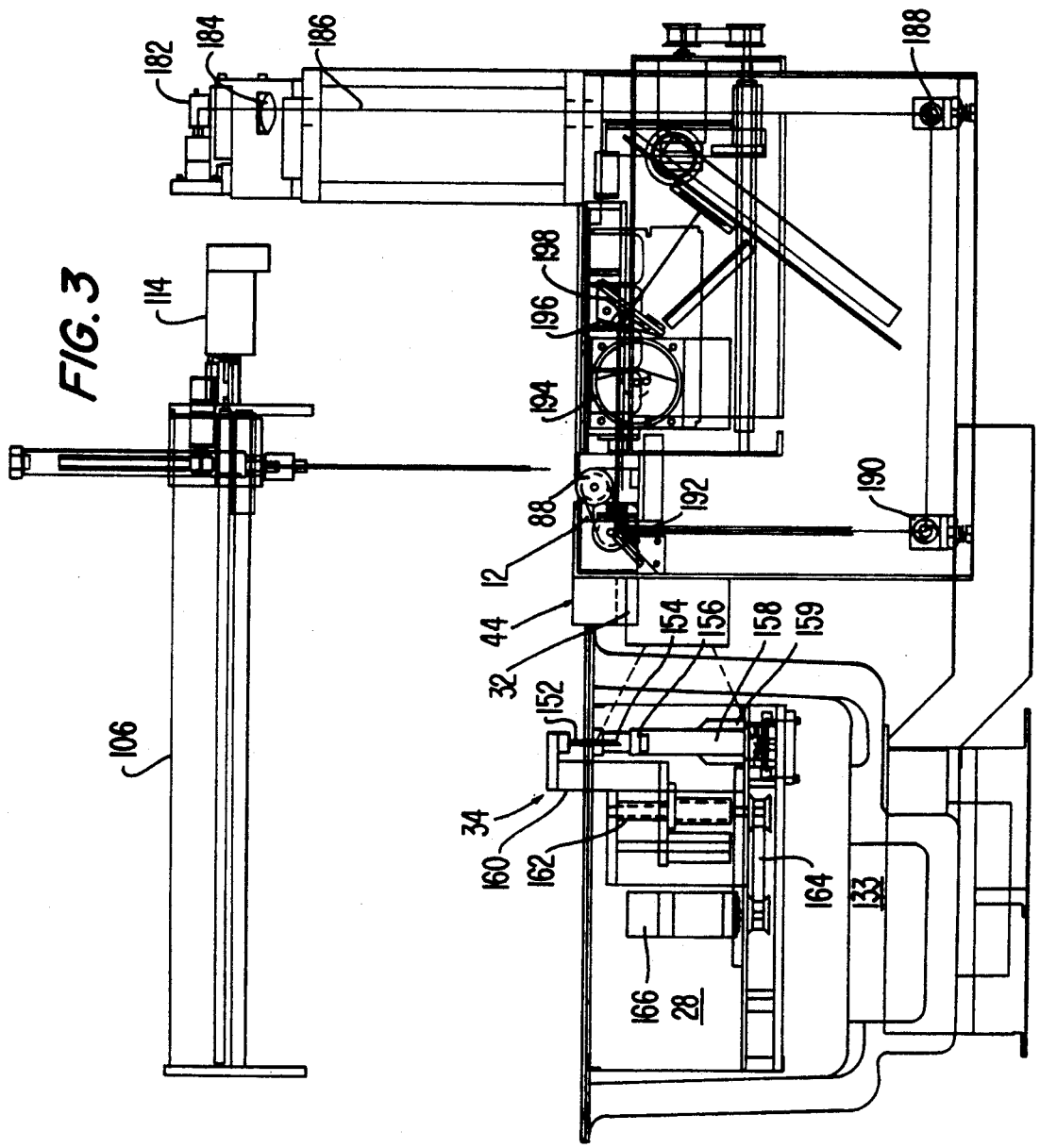
FIG. 3 is a schematic right-side elevation of FIG. 1.

Referring to FIG. 3, piercer 34 includes a piercing tube 152 having a sharp angled end 154, canted at approximately the same angle as the tip of a conventional hypodermic needle, for piercing a septum 156 of an evacuated collection tube 158. Piercing tube 152 is mounted in a support 160 which engages a vertical lead screw 162 which is connected by way of a belt and pulley system 164 to a motor 166 for driving lead screw 162. With appropriate movement of lead screw 162, piercing tube 152 is caused to be lowered for piercing septum 156 or to be removed therefrom. A holding mechanism 159 holds tube 158 in place while piercing tube 152 is inserted and withdrawn. Piercer 34 has an opening 168 (FIG. 1) at the top concentrically aligned with piercing tube 152, so that when sample probe 36 is aligned with piercing tube 152 a pathway is provided for lowering the sample probe into an evacuated collection tube 158, for aspirating a fluid sample therefrom.

Figure 5:
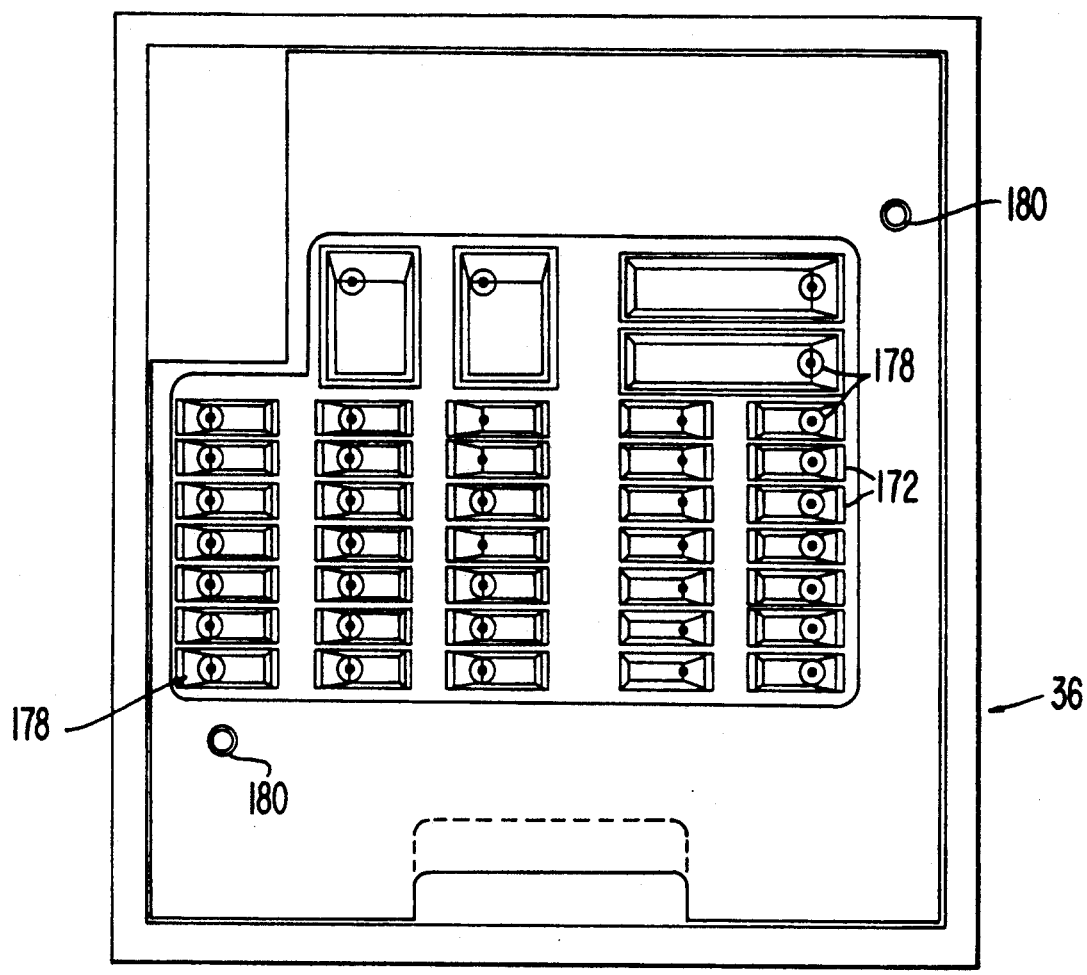
FIG. 5 is a top elevation of the reagent container block of FIG. 1.
Figure 6:
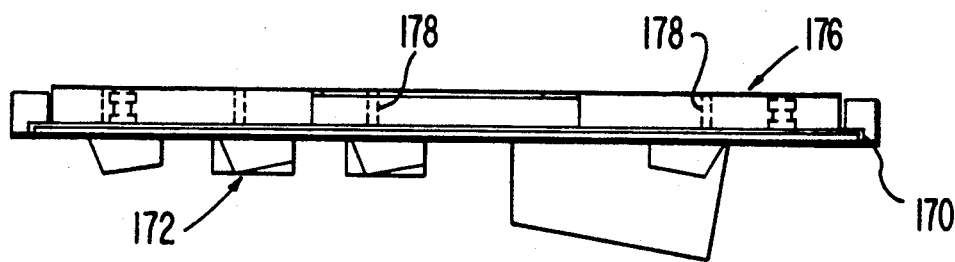
FIG. 6 is a side elevation of FIG. 5.

Reagent chamber 35 is shown in greater detail in FIGS. 5 and 6. As shown in these Figures, a reagent container support plate or tray 170, is provided for supporting a plurality of reagent containers or cups 172, of varying capacities. A reagent cover 176, of approximately one half inch thickness, is placed over reagent container support plate 170. Reagent cover 176 is provided with reagent probe holes 178 positioned above respective ones of reagent containers 172. Probe holes have a diameter (approximately 3 mm) slightly larger than the diameter of reagent probes 40 and 42 for permitting the probes to be lowered into selected ones of the reagent containers. Reagent cover 176 serves as an anti-evaporation cover for retarding or preventing evaporation of the reagents in reagent containers 172 while still allowing access to the reagents through probe holes 178. The anti-evaporation cover additionally serves to retard rapid temperature shifts by providing a barrier between different temperature zones. Although there are multiple holes in the anti-evaporation cover, it is of sufficient depth to provide the tortuosity necessary to retard or prevent evaporation of liquids. Desirably, reagent cover 176 is provided with locator pins 180 for accurately positioning the cover over the reagent containers and in alignment with the horizontal tracks of reagent probes 38, 40 and 42.

Probe washing station 44, comprises a trough 210, containing a cleaning solution such as bleach. An additional trough 212 is provide for receiving waste fluids and cleaning solution from the probes during the washing process. Trough 212 is provided with a plurality of riser platforms 214, 216, 218 and 220, each containing a concave recess and serving as a deflector for fluid and cleaning solution expelled from a probe. After a probe dispenses its fluid into a reaction well in a cuvette, and before the probe is positioned to aspirate sample or reagent as the case may be, the probe is positioned over trough 210 for aspirating cleaning solution The probe is then positioned over the corresponding deflector where primer fluid, such as water, is forced through the probe interior for expelling the cleaning solution, followed by primer liquid, against the deflector thereby creating a fountain effect which washes the outside of the probe. The waste solutions are captured by trough 212 and vented away through a waste outlet (not shown). A more detailed description of probe washing station 44 is described in the aforementioned U.S. Pat. No. 4,989,623 to Hoffman et al.

Figure 2:
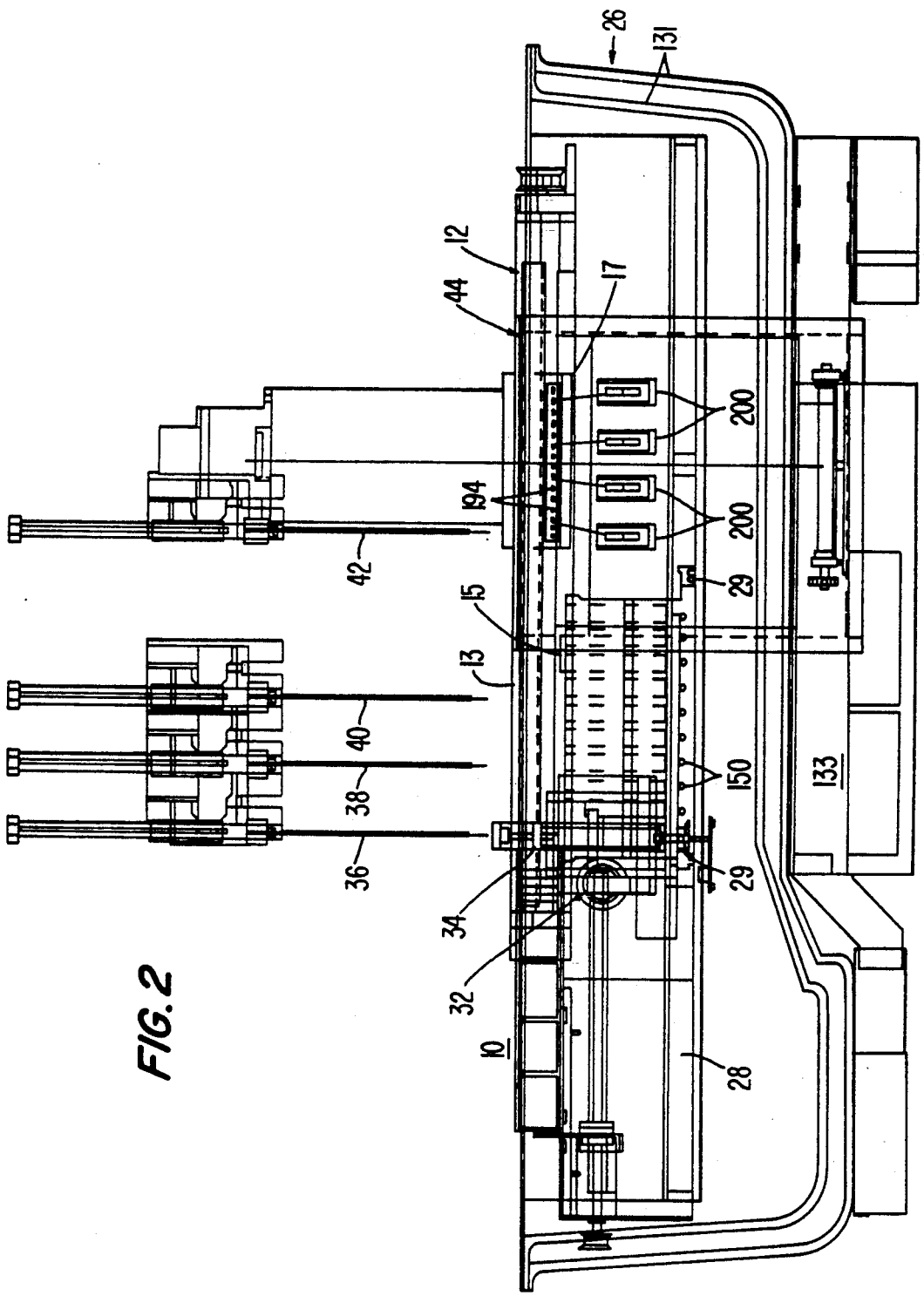
FIG. 2 is a schematic front elevation of FIG. 1.

Optical monitoring station 22 comprises a multichannel optical monitoring system of the type described in detail in the above-mentioned U.S. Pat. No. 5,002,392 to Swope et al. Briefly, and with reference to FIGS. 2 and 3, the optical monitoring system includes a broad band light source 182, which passes light through a slit (not shown). A collimating lens 184, collimates the beam to form a slowly diverging beam 186 which is folded by reflecting mirrors 188, 190 and 192. Following mirror 192 is a mask (not shown), which includes a plurality of linear-ally spaced apertures for dividing beam 186 into a corresponding number of beams, each defining an optical path or channel 194, as schematically illustrated in FIG. 2. The optical paths or channels 194 are linearally spaced along the track of cuvette transport mechanism 12 so that each reaction well of a cuvette passes from channel-to-channel as cuvette transport mechanism 12 incrementally advances the cuvettes along the linear path. The light beams passing through the reaction wells of the cuvettes are passed through a rotating shutter 194 which sequentially passes the light beams to diffraction gratings 196 where the beams are diffracted and focused by focusing lenses 198 onto respective photodiode arrays 200 which are subsequently electronically scanned for reading electronic signals which correspond to the spectral distribution of the beams transmitted by the respective reaction volumes contained in the reaction wells of the cuvettes. In one specific implementation, the optical monitoring system includes 20 channels, and the rotating shutter operates to sequentially pass the beams within groups of five beams, so that only one beam from each group of five beams is passed onto a photodiode array at any one time. The focusing lenses operate to focus each group of five beams onto a respective one of photodiode arrays 200.

The operation of the sample handling system will now be described in the context of one specific implementation of the invention, it being understood that the invention is not limited to this particular implementation.

Operation of the sample handling system according to the invention is centered on linear track 13 along which cuvettes are advanced from station to station by lead screw 88. The basic timing and sequencing of the system is based on advancing the cuvettes along the linear track a distance equal to the distance between successive reaction wells.

Initially, an operator loads cuvettes into the instrument by placing a cassette of cuvettes into cassette frame 46. Each cassette holds, for example, 120 cuvettes. The cuvettes are automatically moved from the cassette onto linear track 13 by arm 52 where they engage lead screw 88. Each cuvette preferably has four ¼ inch reaction wells. Lead screw 88 is activated every fifteen seconds to move the cuvettes in 0.25 inch increments in 0.1 seconds. The instrument controller monitors each cuvette by the timing associated with the lead screw. Lead screw 88 advances the cuvettes to the first station, i.e., sample insertion station 14, where a sample is delivered to a reaction well aligned with sample probe 36. Two minutes later, the reaction well of the cuvette arrives at the first reagent delivery probe 38 where diluent or a reagent is added, depending on the test being carried out. The second reagent probe 40 is located at the four minute position where an activator can be added. Five minutes later the loaded reaction well of the cuvette reaches the third reagent probe 42 where a reagent is added and the reaction monitoring begins. The reaction is monitored electro-optically by optical monitoring system 22 which measures changes in the optical transmission of the reaction volume as the clot forms or as the chromometric reaction proceeds. As the cuvette is moved along the track, the optical monitoring continues for twenty consecutive stations, that is, for 300 seconds. Following the optical monitoring station the cuvette leaves the track and is sent to a waste container (not shown).

Patient plasma samples are stored in refrigerated housing 26 in the original evacuated blood collection tubes used to obtain the patient's sample which has been previously spun down to obtain the plasma and bar-coded for patient identification and test protocol to be performed. The evacuated sample collection tubes are placed in the holders of shuttles 28 and advanced by the shuttle drive mechanism to the bar code reader. The evacuated sample collection tubes can be arranged in any order since the bar code on each sample collection tube allows the instrument to automatically correlate a patient with a given sample. The bar code read by bar code reader 32 also programs the instrument controller for determining the amount of sample to be aspirated by sample probe 36, the number of reaction wells to be filled with the sample, and the amounts and types of reagents/buffers/additives/activators to be injected into the respective reaction wells by reagent probes 38, 40 and 42. Subsequent to programming station 30, a sample collection tube is advanced to piercer 34 where piercing tube 152 is caused to pierce the septum of the evacuated sample tube to allow sample probe 36 to be lowered into the sample collection tube to aspirate a programmed amount of sample. Sample probe 36 is next removed from the evacuated sample collection tube and horizontally moved over a reaction well positioned at sample insertion station 14 and lowered into the reaction well where a programmed amount of sample is expelled into the reaction well. The evacuated sample collection tubes can be removed from refrigerated housing 26 at any time after sample aspiration is complete; however, because the samples are maintained at lowered temperatures, they can be retained for further testing without having to be immediately removed from its shuttle. Reagent chamber 35 stores various controls, diluents, activators and reagents. In one implementation of the system up to twenty-two containers of these materials are stored in reagent chamber 35. All containers are held to a temperature of about 7° C. and the reagents are heated, if necessary, in the reagent probe as they are being dispensed.

Pumping in all cases is performed with positive displacement syringe pumps operatively connected with respective ones of the probe. No manipulation of pump tubing is required as is the case with peristaltic pumps. A reagent is dispensed into a reaction well in a manner that promotes mixing with the sample and other contents of the reaction well. The reagent temperature and volume are controlled by the instrument controller.

Desirably, fluid level sensing is utilized to control the height of a reagent probe relative to the level of a reagent in its container and relative to the contents of a reaction well. This permits bringing the outside of a probe into contact with a minimum quantity of reagent. This, in turn, reduces the possibility for carry-over. Additionally, level sensing is used to control the height of a probe above the fluid level while dispensing in order to minimize carry-over and to maximize mixing.

It will be understood that the above description of the present invention is susceptible to various modifications, changes and adaptations, and the same are intended to be comprehended within the meaning and range of equivalents of the appended claims.

What is claimed is:

1. An arrangement for temperature regulating a fluid sample in a cuvette transported through various stations of an automated system for optically monitoring the sample in the cuvette, comprising:
   a track for guiding the cuvette through the various stations of the optical monitoring system, the sample being in heat exchange relationship with said track through the cuvette, said track including first and second adjacent portions which are temperature controlled;
   drive means for driving the cuvette along said track;
   cooling means for cooling the first portion of said track;
   heating means for heating the second portion of said track; and heat flow restriction means located between said first and second adjacent portions of the track for restricting heat flow between said first and second adjacent portions of the track.

2. An arrangement as defined in claim 1, wherein said track comprises a continuous element having a smooth surface for sliding engagement with the cuvette.

3. An arrangement as defined in claim 2, wherein said heat flow restriction means comprises a third portion of said track between said first and second portions and having a more narrow cross section than said first and second portions.

4. An arrangement as defined in claim 1, wherein said track is linear.

* * * * *